United States Patent
Gutman et al.

(10) Patent No.: US 7,723,514 B2
(45) Date of Patent: *May 25, 2010

(54) METHOD OF PREPARING A 5H-DIBENZ(B,F)AZEPINE-5-CARBOXAMIDE

(75) Inventors: Daniella Gutman, Rishon Lezion (IL); Wael Baidossi, Hamesholash (IL)

(73) Assignee: Taro Pharmaceuticals U.S.A., Inc., Hawthorne, NY (US)

(*) Notice: Subject to any disclaimer, the term of this patent is extended or adjusted under 35 U.S.C. 154(b) by 965 days.

This patent is subject to a terminal disclaimer.

(21) Appl. No.: 11/427,503

(22) Filed: Jun. 29, 2006

(65) Prior Publication Data

US 2006/0241292 A1    Oct. 26, 2006

Related U.S. Application Data

(63) Continuation of application No. 10/460,946, filed on Jun. 13, 2003, now Pat. No. 7,091,339.

(60) Provisional application No. 60/388,811, filed on Jun. 14, 2002.

(51) Int. Cl.
C07D 223/18 (2006.01)

(52) U.S. Cl. ........................................ 540/589

(58) Field of Classification Search ................ 540/589
See application file for complete search history.

(56) References Cited

U.S. PATENT DOCUMENTS

| | | | |
|---|---|---|---|
| 5,808,058 A | 9/1998 | Milanese et al. | |
| 6,670,472 B2 | 12/2003 | Ansari et al. | |
| 7,091,339 B2 * | 8/2006 | Gutman et al. | 540/589 |
| 2003/0105076 A1 | 6/2003 | Ansari et al. | |

FOREIGN PATENT DOCUMENTS

| | | |
|---|---|---|
| EP | 0688768 A1 | 12/1995 |
| EP | 0 847 390 B1 | 8/2000 |
| EP | 1 302 464 A1 | 4/2003 |
| WO | WO-96/21649 A1 | 7/1996 |
| WO | WO-97/38978 A1 | 10/1997 |
| WO | WO-01/56992 A2 | 8/2001 |
| WO | WO-02/064557 A2 | 8/2002 |

OTHER PUBLICATIONS

International Search Report for International Application No. PCT/US03/18823, 2004.

Supplemental Search Report for European Patent Application No. 03734588.1, mailed on Nov. 18, 2009.
English Language Abstract of EP 0688768 (Dec. 27, 1995) from EPO website (Accessed Jan. 11, 2010).
Machine Translation of EP 0688768 (Dec. 27, 1995), from EPO website (Accessed Jan. 11, 2010).

* cited by examiner

*Primary Examiner*—Brenda L Coleman
(74) *Attorney, Agent, or Firm*—Venable LLP; Zayd Alathari; Michael A. Gollin

(57) ABSTRACT

The present invention provides a method of preparing a 5H-dibenz[b,f]azepine-5-carboxamide of formula (1)

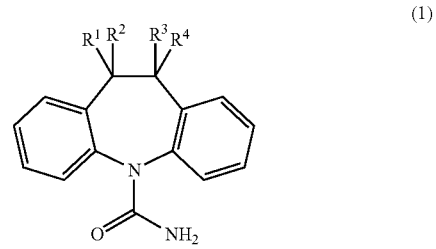

(1)

wherein $R^1$, $R^2$, $R^3$, and $R^4$ are independently selected from the group consisting of hydrogen, halogen, nitro, cyano, carboxyl, A, —CO(A), —OCO(A), —O(A), —N(A)$_2$, —CON(A)$_2$, and —COO(A), wherein A is selected from the group consisting of $C_1$-$C_{10}$ alkyl, $C_3$-$C_{10}$ cycloalkyl, $C_2$-$C_{10}$ alkenyl, $C_5$-$C_{10}$ cycloalkenyl, $C_2$-$C_{10}$ alkynyl, and $C_6$-$C_{20}$ aryl, wherein the two A groups of —N(A)$_2$ and —CON(A)$_2$ can be the same or different, and wherein $R^2$ and $R^3$ can together form a bond; comprising reacting a 5H-dibenz[b,f]azepine of formula (2)

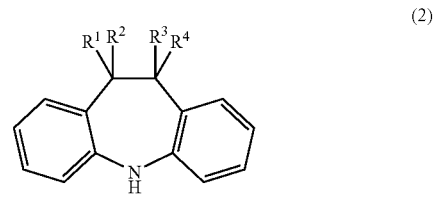

(2)

with a) a cyanate salt selected from the group consisting of alkali metal cyanate salts and alkaline-earth metal cyanate salts, and b) a salt of an amino compound having no N—H bonds, wherein the salt has a $K_a$ (25° C.) of at least about $10 \times 10^{-11}$.

10 Claims, No Drawings

METHOD OF PREPARING A 5H-DIBENZ(B,F)AZEPINE-5-CARBOXAMIDE

RELATED APPLICATIONS

This application is a continuation of U.S. application Ser. No. 10/460,946, filed Jun. 13, 2003, which claims the benefit of U.S. Provisional Application No. 60/388,811, filed Jun. 14, 2002, the disclosure of which is incorporated herein by reference in its entirety.

BACKGROUND OF THE INVENTION

1. Field of the Invention

This invention provides a method of preparing a heterocyclic carbon compound containing, as the sole ring heteroatom, a nitrogen atom attached to two benzene rings. More specifically, the invention provides a method of preparing a 5H-dibenz[b,f]azepine-5-carboxamide.

2. Description of Related Art 10-oxo-10,11-dihydro-5H-dibenz[b,f]azepine-5-carboxamide (oxcarbazepine) is used to control some types of seizures in the treatment of epilepsy (Ziao, K., Reiner, J., and Xie, W., Frontiers of Biotechnology & Pharmaceuticals, 2:331-332). A number of methods to synthesize oxcarbazepine are known. For example, U.S. Pat. No. 5,808,058 (the '058 patent) discloses the following reaction scheme for the preparation of oxcarbazepine:

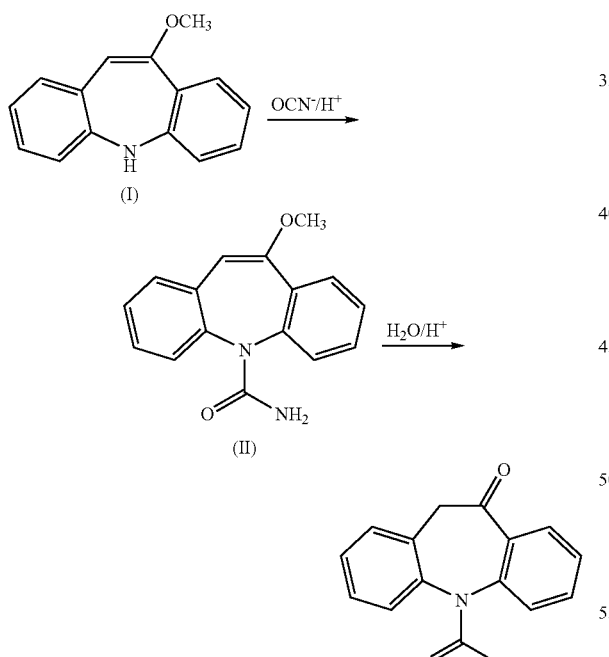

In this process, oxcarbazepine (III) is prepared by direct carbamoylation with isocyanic acid generated in situ from an alkali or alkaline-earth metal cyanate and a mineral or carboxylic acid, followed by acid hydrolysis of the enol ether (II). In each working example, the carbamoylation reaction was conducted at a temperature of ≧40° C., and took at least 4-24 hours.

The concentrated acid reagents employed in the method of the '058 patent are caustic and must be handled with extreme care. Moreover, many of the suggested acids, such as trichloroacetic acid, are costly.

According to EP 1 302 464 A1 (the '464 application), another drawback of the carbamoylation reaction disclosed in the '058 patent is that it creates a number of byproducts that make it difficult to purify the prepared oxcarbazepine. The '464 application attempts to solve that problem by replacing the mineral acid or carboxylic acid of the '058 patent with an aromatic carboxylic acid, such as benzoic acid. However, each example in the '464 application was performed at a temperature of at least 85° C., and reported yields were only 28% to 49%.

A need exists for a method of preparing a 5H-dibenz[b,f]azepine-5-carboxamide from safe, inexpensive, easy to handle reagents, wherein the reaction proceeds in high yield without producing byproducts that are difficult to separate.

SUMMARY OF THE INVENTION

The present invention provides a method of preparing a 5H-dibenz[b,f]azepine-5-carboxamide in high yield and purity using inexpensive reagents that are safe and easy to handle. More specifically, the invention provides a method of preparing a 5H-dibenz[b,f]azepine-5-carboxamide of formula (1)

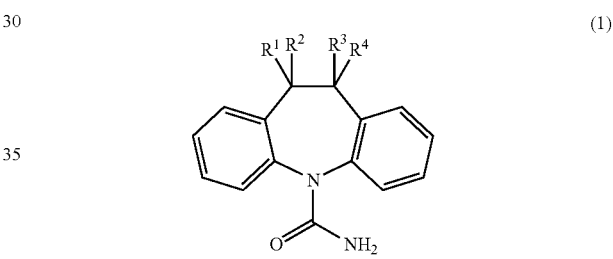

wherein $R^1$, $R^2$, $R^3$, and $R^4$ are independently selected from the group consisting of hydrogen, halogen, nitro, cyano, carboxyl, A, —CO(A), —OCO(A), —O(A), —N(A)$_2$, —CON(A)$_2$, and —COO(A), wherein A is selected from the group consisting of $C_1$-$C_{10}$ alkyl, $C_3$-$C_{10}$ cycloalkyl, $C_2$-$C_{10}$ alkenyl, $C_5$-$C_{10}$ cycloalkenyl, $C_2$-$C_{10}$ alkynyl, and $C_6$-$C_{20}$ aryl, wherein the two A groups of —N(A)$_2$ and —CON(A)$_2$ can be the same or different, and wherein $R^2$ and $R^3$ can together form a bond; comprising reacting a 5H-dibenz[b,f]azepine of formula (2)

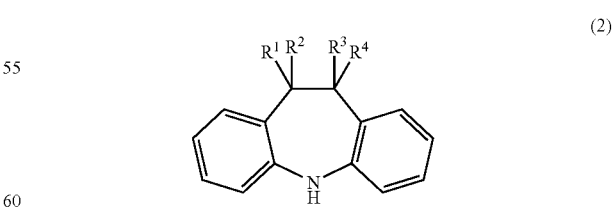

with a) a cyanate salt selected from the group consisting of alkali metal cyanate salts and alkaline-earth metal cyanate salts, and b) a salt of an amino compound having no N—H bonds, wherein the salt has a $K_a$ (25° C.) of at least about $10 \times 10^{-11}$.

DETAILED DESCRIPTION OF THE INVENTION

The present invention provides a method of preparing a 5H-dibenz[b,f]azepine-5-carboxamide of formula (1)

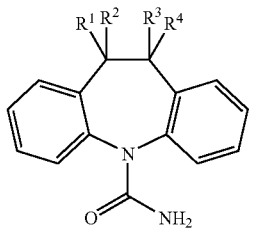

(1)

wherein $R^1$, $R^2$, $R^3$, and $R^4$ are independently selected from the group consisting of hydrogen, halogen, nitro, cyano, carboxyl, A, —CO(A), —CO(A), —O(A), —N(A)$_2$, —CON(A)$_2$, and —COO(A), wherein A is selected from the group consisting of $C_1$-$C_{10}$ alkyl, $C_3$-$C_{10}$ cycloalkyl, $C_2$-$C_{10}$ alkenyl, $C_5$-$C_{10}$ cycloalkenyl, $C_2$-$C_{10}$ alkynyl, and $C_6$-$C_{20}$ aryl, wherein the two A groups of —N(A)$_2$ and —CON(A)$_2$ can be the same or different, and wherein $R^2$ and $R^3$ can together form a bond; comprising reacting a 5H-dibenz[b,f]azepine of formula (2)

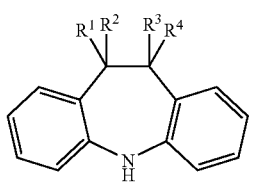

(2)

with a) a cyanate salt selected from the group consisting of alkali metal cyanate salts and alkaline-earth metal cyanate salts, and b) a salt of an amino compound having no N—H bonds, wherein the salt has a $K_a$ (25° C.) of at least about $10 \times 10^{-11}$.

Preferably, A is $C_1$-$C_{10}$ alkyl. Still more preferably, A is $C_1$-$C_6$ alkyl.

The above-described alkyl, cycloalkyl, alkenyl, cycloalkenyl, alkynyl, and aryl groups may each be substituted by up to four moieties selected from the group consisting of nitrogen-containing moieties (e.g., amino, amido, etc.), oxygen-containing moieties (e.g., hydroxyl, carboxyl, etc.), halogens, and sulfur-containing moieties (e.g., thiol, sulfonyl, etc.).

When $R^1$, $R^2$, $R^3$, and/or $R^4$ comprise an alkyl, cycloalkyl, alkenyl, cycloalkenyl, alkynyl, and/or aryl group that is substituted with a nucleophilic moiety, such as an amino, hydroxyl, or thiol moiety, it is preferred that the nucleophilic moiety be protected with a suitable protecting group. A suitable protecting group will prevent the nucleophilic moiety from reacting with the electrophilic cyanic acid reagent (which we believe is generated in situ by the reaction of the cyanate salt with the salt of the amino compound having no N—H bonds). Also, it will be possible to remove a suitable protecting group from the nucleophilic moiety after conducting the method of the present invention. A compilation of suitable protecting groups can be found in Theodora W. Greene & Peter G. M. Wuts, Protective Groups in Organic Synthesis (3d ed, 1999), which is incorporated herein by reference in its entirety. Examples include t-butyloxycarbonyl and benzyl for an amino moiety, methoxymethyl and t-butyldimethylsilyl for a hydroxyl moiety, and t-butyloxycarbonyl and benzoyl for a thiol moiety, According to the present invention, when $R^1$, $R^2$, $R^3$, and/or $R^4$ comprise an alkyl, cycloalkyl, alkenyl, cycloalkenyl, alkynyl, or aryl group that possesses a moiety, including a non-nucleophilic moiety, that is protected with a protecting group, the protecting group is not considered part of the alkyl, cycloalkyl, alkenyl, cycloalkenyl, alkynyl, or aryl group insofar as the atom limitations expressed above are concerned. In other words, the constituent atoms of the protecting group have no bearing on whether the alkyl, cycloalkyl, alkenyl, cycloalkenyl, alkynyl, or aryl group has a particular number of carbon atoms or other moieties. For example, when $R^1$ is 5-(t-butyldimethylsilyloxy)pentyl, the six carbon atoms and one silicon atom of the t-butyldimethylsilyl (TBS) protecting group have no bearing on the total number of carbon atoms or other moieties in $R^1$. Thus, according to the present invention, the 5-(t-butyldimethylsilyloxy)pentyl group is an alkyl group (pentyl) having five carbon atoms, and one oxygen-containing moiety (hydroxyl). In other words, according to the present invention, the 5-(t-butyldimethylsilyloxy)pentyl group is not an alkyl group having eleven carbon atoms and one oxygen-containing moiety.

Other examples of $C_1$-$C_{10}$ alkyl groups include methyl ($C_1$), isobutyl ($C_4$), and 4-(benzyloxy)butyl ($C_4$ with an oxygen-containing moiety (hydroxyl)—the benzyl group is a protecting group). Examples of $C_3$-$C_{10}$ cycloalkyl groups include cyclopentyl ($C_5$), 2-(methyl)cyclohexyl ($C_7$), and 2-(N,N-(dibenzyl)amino)cyclohexyl ($C_6$ with a nitrogen-containing moiety (amino)—the benzyl groups are protecting groups). Examples of $C_2$-$C_{10}$ alkenyl groups include allyl ($C_3$), 2-methyl-2-butenyl ($C_5$), and 3-hexen-5-one-2-yl ($C_6$ with an oxygen-containing moiety (ketone)). Examples of $C_5$-$C_{10}$ cycloalkenyl groups include cyclopentenyl ($C_5$), 4-(isopropyl)cyclohexenyl ($C_9$), and 4-(chloromethyl)cyclohexenyl ($C_7$ with a halogen (chlorine)). Examples of $C_2$-$C_{10}$ alkynyl groups include 2-butynyl ($C_4$), 4-phenyl-2-butynyl ($C_{10}$), and 4-bromomethyl-2-pentynyl ($C_6$ with a halogen (bromine)). Examples of $C_6$-$C_{20}$ aryl groups include phenyl ($C_6$), 2-(methyl)naphthyl ($C_{11}$), and 3-(cyano)isoquinolynyl ($C_{10}$ with two nitrogen-containing moieties (cyano and the ring nitrogen)).

According to a preferred embodiment of the present invention, $R^1$, $R^2$, $R^3$, and $R^4$ are independently selected from the group consisting of hydrogen, halogen, A, —OCO(A), —O(A), and —N(A)$_2$, and $R^2$ and $R^3$ can together form a bond. According to a more preferred embodiment, $R^1$, $R^2$, $R^3$, and $R^4$ are independently selected from the group consisting of hydrogen, halogen, —OCO(A), —O(A), and —N(A)$_2$, and $R^2$ and $R^3$ can together form a bond.

It is preferred that $R^2$ and $R^3$ together form a bond. It is especially preferred that $R^2$ and $R^3$ together form a bond, $R^1$ is hydrogen, and $R^4$ is hydrogen or —O(A), with —OCH$_3$ being a preferred example of —O(A). The invention thus provides a method of preparing a 5H-dibenz[b,f]azepine-5-carboxamide of formula (3)

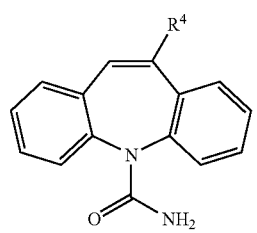

(3)

wherein $R^4$ is selected from the group consisting of hydrogen and —O(A), wherein A is selected from the group consisting of $C_1$-$C_{10}$ alkyl, $C_3$-$C_{10}$ cycloalkyl, $C_2$-$C_{10}$ alkenyl, $C_5$-$C_{10}$ cycloalkenyl, $C_2$-$C_{10}$ alkynyl, and $C_6$-$C_{20}$ aryl; comprising reacting a 5H-dibenz[b,f]azepine of formula (4)

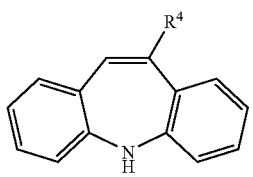

(4)

with:
- a. a cyanate salt selected from the group consisting of alkali metal cyanate salts and alkaline-earth metal cyanate salts, and
- b. a salt of an amino compound having no N—H bonds, wherein the salt has a $K_a$ (25° C.) of at least about $10 \times 10^{-11}$.

When $R^4$ is hydrogen, the 5H-dibenz[b,f]azepine-5-carboxamide of formula (3) is 5H-dibenz[b,f]azepine-5-carboxamide (carbamazepine). When $R^4$ is —O(A) (e.g., —OCH$_3$), the 5H-dibenz[b,f]azepine-5-carboxamide of formula (3) is a 10-alkoxy-5H-dibenz[b,f]azepine-5-carboxamide, which can be hydrolyzed with aqueous acid to form 10-oxo-10,11-dihydro-5H-dibenz[b,f]azepine-5-carboxamide (oxcarbazepine).

According to one embodiment, when $R^4$ is hydrogen, the salt of an amino compound having no N—H bonds is a pyridinium salt. In another embodiment, when $R^4$ is —O(A), the salt of an amino compound having no N—H bonds is a pyridinium salt.

The invention also provides a method of preparing a 5H-dibenz[b,f]azepine-5-carboxamide of formula (3)

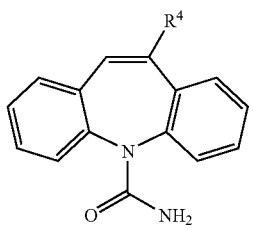

(3)

wherein $R^4$ is selected from the group consisting of hydrogen and —O(A), wherein A is $C_1$-$C_{10}$ alkyl; comprising reacting a 5H-dibenz[b,f]azepine of formula (4)

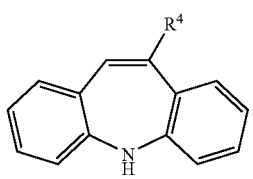

(4)

with:
- a. a cyanate salt selected from the group consisting of alkali metal cyanate salts and alkaline-earth metal cyanate salts, and
- b. a salt of an amino compound having no N—H bonds, wherein the salt has a $K_a$ (25° C.) of at least about $10 \times 10^{-11}$.

When $R^4$ is —O(A) (e.g., —OCH$_3$), the 5H-dibenz[b,f]azepine-5-carboxamide of formula (3) is a 10-alkoxy-5H-dibenz[b,f]azepine-5-carboxamide, which can be hydrolyzed with aqueous acid to form 10-oxo-10,11-dihydro-5H-dibenz[b,f]azepine-5-carboxamide (oxcarbazepine). In one embodiment, when $R^4$ is —O(A), the salt of an amino compound having no N—H bonds is a pyridinium salt.

Examples of suitable alkali and alkaline-earth metal cyanate salts include NaOCN and KOCN, with NaOCN being preferred.

Examples of suitable salts of amino compounds having no N—H bonds, wherein the salt has a $K_a$ (25° C.) of at least about $10 \times 10^{-11}$, include salts formed by the reaction between a) an acid selected from the group consisting of hydrobromic acid, hydrochloric acid, p-toluenesulfonic acid, trifluoromethanesulfonic acid, trifluoroacetic acid, and 3-nitrobenzenesulfonic acid; and b) an amino compound having no N—H bonds selected from the group consisting of pyridine, 2-methylpyridine, 3-methylpyridine, 4-methylpyridine, 2,3-dimethylpyridine, 2,4-dimethylpyridine, 3,5-dimethylpyridine, N,N-dimethylaniline, isoquinoline, acridine, 1-methylimidazole, and 1-methylbenzimidazole. It is preferred that the salt of an amino compound having no N—H bonds comprise one molecule of the acid and one molecule of the amino compound having no N—H bonds—i.e., a 1:1 salt.

Further examples of suitable salts of amino compounds having no N—H bonds, wherein the salt has a $K_a$ (25° C.) of at least about $10 \times 10^{-11}$, include salts formed by the reaction between a) an acid selected from the group consisting of hydrobromic acid, hydrochloric acid, p-toluenesulfonic acid, trifluoromethanesulfonic acid, trifluoroacetic acid, and 3-nitrobenzenesulfonic acid; and b) an amino compound having no N—H bonds selected from the group consisting of 1,3,5-triazine, pyrazine, quinoline, pyrimidine, pyridazine, 1-methylpyrrole, 1methylindole, and thiazole.

Thus, the invention provides a method of preparing a 5H-dibenz[b,f]azepine-5-carboxamide of formula (1)

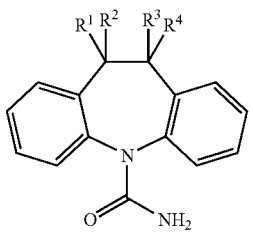

(1)

wherein $R^1$, $R^2$, $R^3$, and $R^4$ are independently selected from the group consisting of hydrogen, halogen, nitro, cyano, carboxyl, A, —CO(A), —OCO(A), —O(A), —N(A)$_2$, —CON(A)$_2$, and —COO(A), wherein A is selected from the group consisting of $C_1$-$C_{10}$ alkyl, $C_3$-$C_{10}$ cycloalkyl, $C_2$-$C_{10}$ alkenyl, $C_5$-$C_{10}$ cycloalkenyl, $C_2$-$C_{10}$ alkynyl, and $C_6$-$C_{20}$ aryl, wherein the two A groups of —N(A)$_2$ and —CON(A)$_2$ can be the same or different, and wherein $R^2$ and $R^3$ can together form a bond; comprising reacting a 5H-dibenz[b,f]azepine of formula (2)

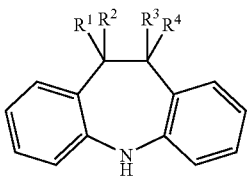

(2)

with:
a. a cyanate salt selected from the group consisting of alkali metal cyanate salts and alkaline-earth metal cyanate salts, and
b. a salt of an amino compound having no N—H bonds, wherein the salt is formed by the reaction between:
(i) an acid selected from the group consisting of hydrobromic acid, hydrochloric acid, p-toluenesulfonic acid, trifluoromethanesulfonic acid, trifluoroacetic acid, and 3-nitrobenzenesulfonic acid; and
(ii) an amino compound having no N—H bonds selected from the group consisting of pyridine, 2-methylpyridine, 3-methylpyridine, 4-methylpyridine, 2,3-dimethylpyridine, 2,4-dimethylpyridine, 3,5-dimethylpyridine, N,N-dimethylaniline, isoquinoline, acridine, 1-methylimidazole, 1-methylbenzimidazole, 1,3,5-triazine, pyrazine, quinoline, pyrimidine, pyridazine, 1-methylpyrrole, 1-methylindole, and thiazole.

The salt of an amino compound having no N—H bonds may be preformed. According to the present invention, a salt of an amino compound having no N—H bonds is "preformed" if its constituent parts—the acid and the amino compound having no N—H bonds—are combined prior to their use in the method of the present invention. For example, several preformed salts of amino compounds having no N—H bonds are commercially available, such as pyridinium bromide, pyridinium chloride, pyridinium tribromide, and pyridinium-p-toluenesulfonate (e.g., from Sigma-Aldrich Corp. (St. Louis, Mo.)). An example of how to prepare a preformed salt of an amino compound having no N—H bonds is provided in Example 6 below.

The salt of an amino compound having no N—H bonds also may be formed in situ by combining its constituent parts—the acid and the amino compound having no N—H bonds—during the method of the present invention. For example, an amino compound having no N—H bonds can be added to a solution comprising the compound of formula (2) and a cyanate salt, and an acid added thereto. When the amino compound having no N—H bonds is formed in situ, it is preferred that less than one molar equivalent of acid be used, based on the molar quantity of the amino compound having no N—H bonds.

We attempted to convert 10-methoxy-5H-dibenz[b,f] azepine (compound of formula (4), wherein $R^4$ is methoxy (2 g, 0.0079 mol)) into 10-methoxy-5H-dibenz[b,f]azepine-5-carboxamide by combining sodium cyanate (2 g, 0.031 mol) and triethylamine hydrochloride (2.8 g, 0.020 mol) in toluene (20 ml). After stirring for about 7 hours at room temperature, thin-layer chromatography (TLC) indicated no discernible conversion to 10-methoxy-5H-dibenz[b,f]azepine-5-carboxamide. Without wishing to be held to any particular theory, we believe it possible that the reaction was unsuccessful because the triethylamine hydrochloride did not convert a sufficient quantity of the cyanate salt to cyanic acid. The $K_a$ (25° C.) of protonated triethylamine (i.e., a salt of triethylamine) is about $9.8 \times 10^{-12}$; the $K_a$ (25° C.) of cyanic acid (HOCN) is about $3.5 \times 10^{-4}$.

Although it is possible that the reaction with triethylamine hydrochloride and other salts of amino compounds having no N—H bonds that have $K_a$'s of less than about $10 \times 10^{-12}$ would proceed under different reaction conditions (e.g., higher temperatures), it is preferred that the salt of an amino compound having no N—H bonds has a $K_a$ (25° C.) of at least about $10 \times 10^{-11}$. More preferably, the salt of an amino compound having no N—H bonds has a $K_a$ (25° C.) of at least about $10 \times 10^{-10}$. Still more preferably, the salt of an amino compound having no N—H bonds has a $K_a$ (25° C.) of at least about $10 \times 10^{-9}$. Even more preferably, the salt of an amino compound having no N—H bonds has a $K_a$ (25° C.) of at least about $10 \times 10^{-8}$. Most preferably, the salt of an amino compound having no N—H bonds has a $K_a$ (25° C.) of at least about $10 \times 10^{-7}$. Tables of $K_a$ (25° C.) values are readily available to those of ordinary skill in the art (see, e.g., CRC Handbook of Chemistry and Physics (63d ed. 1982-83)). $K_a$ (25° C.) values also may be measured (see, e.g., Cookson, Chem. Rev. 1974, 74, 5-28 and references cited therein).

Protonated pyridine (i.e., a salt of pyridine), which is a preferred example of a salt of an amino compound having no N—H bonds, has a $K_a$ (25° C.) of about $5.6 \times 10^{-6}$. According to one embodiment of the present invention, the salt of an amino compound having no N—H bonds has a $K_a$ (25° C.) of less than about $10 \times 10^{-6}$. Preferably, the salt of an amino compound having no N—H bonds is a pyridinium salt (e.g., pyridinium bromide, pyridinium tribromide, pyridinium p-toluenesulfonate, 2-methylpyridinium bromide, etc.), with pyridinium bromide and pyridinium p-toluenesulfonate being especially preferred, and pyridinium bromide being most preferred.

The method of the present invention may be carried out, for example, by combining the 5H-dibenz[b,f]azepine of formula (2) or (4) with a salt of an amino compound having no N—H bonds in an organic solvent. The cyanate salt is added to the reaction mixture and the reaction is allowed to proceed until complete. The reaction may be performed at any suitable temperature, such as from about 15° to about 80° C. Preferably, the reaction is performed at about room temperature (about 20 to about 25° C.). Even when conducted at room temperature, the reaction is generally complete in about eight hours or less, and often is complete in about four hours or less. According to the invention, a reaction is "complete" if the yield increases by about 1% or less when the reaction is allowed to proceed for a longer period of time.

Examples of suitable organic solvents include acetonitrile, chlorinated solvents, and aromatic solvents. Suitable chlorinated solvents include methylene chloride, chloroform, 1,2-dichloroethane, 1,1,1-trichloroethane, trichloroethylene, and chlorobenzene. Suitable aromatic solvents include toluene, xylene, and benzene. Preferred solvents include toluene and acetonitrile, with toluene being most preferred.

The 5H-dibenz[b,f]azepine-5-carboxamide of formula (1) or (3) that is prepared according to the present invention may be purified using any suitable method, such as by chromatography, slurrying in a suitable solvent system, and/or recrystallization from a suitable solvent system. Likewise, when the 5H-dibenz[b,f]azepine-5-carboxamide of formula (1) or (3) is hydrolyzed to form oxcarbazepine, the oxcarbazepine may be purified using any suitable method, such as by chromatography, slurrying in a suitable solvent system, and/or recrystallization from a suitable solvent system.

The present invention provides a method of preparing a 5H-dibenz[b,f]azepine-5-carboxamide from safe, inexpensive, easy to handle reagents. The reaction proceeds in high yield without the production of difficult to separate byproducts.

EXAMPLES

While the following examples are provided to illustrate the present invention, it will be understood that they are not intended to limit the invention's spirit or scope.

Example 1

Synthesis of Oxcarbazepine

In a three-neck flask (500 ml), equipped with a mechanical stirring apparatus, 15 ml water was introduced, followed by pyridinium bromide (71.75 g, 0.45 mole; Chemadaa' (Nir Yitshak, Israel)), The mixture was stirred at room temperature (22° C.) for about 10 minutes. Then 250 ml toluene was added, followed by 50 g (0.224 mol) of 10-methoxy-5H-dibenz[b,f]azepine (compound of formula (4), wherein $R^4$ is methoxy). [Note: 10-methoxy-5H-dibenz[b,f]azepine may be obtained from iminostilbene according to the process disclosed in U.S. Pat. No. 5,808,058, 10-methoxy-5H-dibenz[b,f]azepine also is commercially available from various suppliers, including Zhejiang Jiuzhiou Pharmaceutical Co., Ltd, (Zhejiang, China), and Ningbo Chongyangtang Biologic Tech Co., Ltd, (Ningbo, China)] NaOCN (45 g, 0.69 mol; OCI Corp., South Korea) was added and the reaction was mixed for about 7-8 hours at room temperature (22° C.). After 7-8 hours, 125 ml of water was added, and the mixture was stirred for about 15 minutes. The resulting solid carbamate of formula (1), 10-methoxy-5H-dibenz[b,f]azepine-5-carboxamide, was filtered and washed with 50 ml of water. The organic layer was separated and washed with water (2×50 ml).

In a 500 ml three necked flask, the organic phase from above was introduced, to which the solid carbamate of formula (1) (10-methoxy-5H-dibenz[b,f]azepine-5-carboxamide) was added to form a slurry. The mixture was heated to 89° C. to clarify the solution, and 250 ml of 10% HCl was added dropwise with stirring. When thin layer chromatography indicated that the intermediate carbamate of formula (1) had been substantially consumed, the reaction mixture was cooled to room temperature and the mixture was stirred at this temperature for 15-30 minutes. The product, 10-oxo-10,11-dihydro-5H-dibenz[b,f]azepine-5-carboxamide (oxcarbazepine), was filtered and the crude oxcarbazepine cake was thoroughly washed with water until the pH reached 6-7. The mixture was then washed with toluene (50 ml), and the solids were dried to yield 34.4 g (0.137 mol) crude oxcarbazepine as a yellow-brown powder (yield relative to (2) is 61%).

The crude oxcarbazepine was slurried in 408 ml of boiling 80:20 isopropanol:water for about 1 hour. The solid was separated by filtration and dried to afford 30.6 g oxcarbazepine (89% purification yield). Further purification was carried out in 765 ml of boiling 80:20 isopropanol:water, hot filtration and cooling to room temperature. Filtration and drying of the solid precipitate afforded 26.5 g of purified oxcarbazepine (yield relative to starting material (2) is 47%, and purification yield is 87%).

Example 2

One-pot Synthesis of Oxcarbazepine

The carbamoylation reaction was performed as in Example 1. After about 7-8 hours of stirring the carbamoylation reaction mixture (containing pyridinium bromide, 10-methoxy-5H-dibenz[b,f]azepine, water, toluene, and NaOCN) at room temperature (22° C.), the mixture was heated to 55-60° C., and 500 ml of 10% HCl was added drop-wise and carefully. The reaction mixture was warmed to reflux (89° C.) for 3-4 hours, and then worked up and purified as in Example 1. 32.8 g (58% yield) of crude oxcarbazepine was obtained. The crude afforded 24.9 g (44% overall yield) of pure oxcarbazepine.

Example 3

Alternate Hydrolysis of 10-methoxy-5H-dibenz[b,f]azepine

The carbamoylation reaction was performed as in Example 1, except that 150 ml toluene was used instead of 250 ml. The resulting solid carbamate of formula (1), 10-methoxy-5H-dibenz[b,f]azepine-5-carboxamide, was isolated as described in Example 1.

In a three necked flask, 330 ml of isopropyl alcohol, 78 ml of 12% HCl, and the solid 10-methoxy-5H-dibenz[b,f]azepine-5-carboxamide were introduced. The mixture was heated to 78°-82° C. for about 1 hour.

When TLC indicated that the carbamate of formula (1) was consumed, the reaction mixture was cooled to room temperature and stirred for 1 hour. The separated solids were filtered and washed with water to provide crude 10-oxo-10,11-dihydro-5H-dibenz[b,f]azepine-5-carboxamide (oxcarbazepine), which was purified as described in Example 1.

Yield relative to starting material of formula (2) was 43-45%.

Example 4

Synthesis of 10-methoxycarbamazepine Using Pyridinium p-toluenesulfonate 10-methoxy-5H-dibenz(b,f)azepine (29.9 g, 0.134 mol) was added to 300 ml acetonitrile in a three-neck flask (500 ml) equipped with a mechanical stirring apparatus. The mixture was stirred at room temperature for 15 minutes, and then NaOCN (18 g, 0.277 mol) was added, followed by pyridinium p-toluenesulfonate (75 g, 0.3 mol). The mixture was stirred at room temperature for about 4 hours, at which time TLC indicated that the reaction was complete (disappearance of 10-methoxy-5H-dibenz(b,f)azepine).

30 ml water was added, and the mixture stirred for 15 minutes. The solids were filtered and the filtrate was concentrated under vacuum. The semi-solid residue was triturated with acetone to provide a creamy solid, which was dried at 80° C. to provide 18 g (0.068 mol, 50% yield) of 10-methoxy-5H-dibenz[b,f]azepine-5-carboxamide (10-methoxycarbamazepine).

Example 5

Synthesis of Carbamazepine

Pyridinium bromide (14.35 g, 0.090 mol) was added to 3 ml water in a 250 ml three necked flask, equipped with mechanical stirrer and thermometer. The mixture was stirred at room temperature (22° C.) for about 10 minutes, and then 50 ml toluene was added, followed by 5H-dibenz[b,f]azepine (10 g, 0.052 mol) and sodium isocyanate (9 g, 0.138 mol). The reaction was stirred at room temperature for about 3-5 hours.

50 ml water was added, and the mixture stirred for 15 minutes. The solid material was filtered, washed with about 50 ml of water, and dried, providing 8.6 g (70%) of 5H-dibenz[b,f]azepine-5-carboxamide (carbamazepine). The product may be recrystallized from 95% ethanol, Example 6

Preparation of Quinoline Hydrochloride

About 16 ml of 32% HCl (0.14 mol) was slowly added (addition time of about 30 minutes) to 20 g quinoline (0.16 mol) at 0° C. (ice bath). The pH after complete addition was about 4-5. The mixture was stirred for about 15 minutes at room temperature.

Toluene was added to the reaction mixture, the flask was fitted with a Dean Stark apparatus, and the water was removed by azeotropic distillation. After the water was removed, the mixture was cooled to room temperature and the solid quinoline hydrochloride was filtered, washed with toluene, and dried.

Example 7

Synthesis of Oxcarbazepine Using Quinoline Hydrochloride

Quinoline hydrochloride (7.5 g, 0.045 mol), 10-methoxy-5H-dibenz[b,f]azepine (5 g, 0.022 mol), sodium isocyanate (5 g, 0.077 mol), and water (1 ml) were combined in 50 ml toluene. The reaction was stilled at room temperature for about 18 hours.

75 ml water was added, and the solid filtered. The toluene filtrate was washed with water (50 ml), and the filtered solid was added thereto to form a slurry. 20 ml of 12% HCl was added to the slurry, and the mixture was refluxed (89° C.) for two hours. The reaction was cooled to room temperature and the solid was filtered and dried to afford 2.26 g (0.0090 mol, 41%) of crude oxcarbazepine, which was recrystallized from a mixture of isopropyl alcohol/water (80:20) to provide 1.92 g (0.0076 mol, 35%) of pure oxcarbazepine.

Numerous references, including patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entirety and to the same extent as if each reference was individually incorporated by reference.

What is claimed is:

1. A process of preparing 10-oxo-10,11-dihydro-5H-dibenz[b,f]azepine-5-carboxamide, comprising the steps of:
    a) reacting 10-methoxy-5H-dibenz[b,f]azepine with pyridinium bromide and sodium cyanate; and
    b) adding an aqueous HCl solution to provide 10-oxo-10,11-dihydro-5H-dibenz[b,f]azepine-5-carboxamide.

2. The process of claim 1, wherein the step a) is performed in toluene.

3. The process of claim 2, wherein the toluene further contains water.

4. The process of claim 3, wherein the toluene and water are present at a vol/vol ratio of about 125:15.

5. The process of claim 1, wherein the step a) is performed at a temperature of about 89° C.

6. The process of claim 1, wherein the aqueous HCl solution is about 10%.

7. The process of claim 1, further comprising the step of:
    c) purifying 10-oxo-10,11-dihydro-5H-dibenz[b,f]azepine-5-carboxamide.

8. The process of claim 7, wherein the purifying step is performed by:
    a') slurrying the mixture in step b) in a mixture of isopropanol and water at a reflux temperature; and
    b') filtering the slurry to provide purified 10-oxo-10,11-dihydro-5H-dibenz[b,f]azepine-5-carboxamide.

9. The process of claim 8, wherein the isopropanol and water are present at a vol/vol ratio of about 80:20.

10. The process of claim 7, further comprising the step of:
    d) drying 10-oxo-10,11-dihydro-5H-dibenz[b,f]azepine-5-carboxamide.

* * * * *